United States Patent
Chang et al.

(10) Patent No.: US 11,618,027 B2
(45) Date of Patent: Apr. 4, 2023

(54) MOLECULAR DIAGNOSTICS APPARATUS

(71) Applicant: Wistron Corp., New Taipei (TW)

(72) Inventors: Yao-Tsung Chang, New Taipei (TW); Wen-Hui Shih, New Taipei (TW); Chen An Sung, New Taipei (TW)

(73) Assignee: WISTRON CORP., New Taipei (TW)

( * ) Notice: Subject to any disclaimer, the term of this patent is extended or adjusted under 35 U.S.C. 154(b) by 409 days.

(21) Appl. No.: 16/892,253

(22) Filed: Jun. 3, 2020

(65) Prior Publication Data

US 2021/0170395 A1 Jun. 10, 2021

(30) Foreign Application Priority Data

Dec. 10, 2019 (TW) .................... 108216368

(51) Int. Cl.
| | |
|---|---|
| *B01L 3/00* | (2006.01) |
| *H02J 7/02* | (2016.01) |
| *H02J 50/12* | (2016.01) |
| *B01L 7/00* | (2006.01) |
| *C12Q 1/686* | (2018.01) |

(52) U.S. Cl.
CPC ............. *B01L 3/5085* (2013.01); *B01L 7/52* (2013.01); *C12Q 1/686* (2013.01); *H02J 7/02* (2013.01); *H02J 50/12* (2016.02); *B01L 2300/023* (2013.01); *B01L 2300/06* (2013.01); *B01L 2300/0627* (2013.01); *B01L 2300/18* (2013.01)

(58) Field of Classification Search
None
See application file for complete search history.

(56) References Cited

U.S. PATENT DOCUMENTS

| | | | | |
|---|---|---|---|---|
| 9,404,151 | B2* | 8/2016 | Chandra | ................... B01L 7/52 |
| 2007/0095393 | A1* | 5/2007 | Zucchelli | ............ F16K 99/0001 |
| | | | | 137/68.11 |
| 2008/0057542 | A1* | 3/2008 | Roberts | ..................... B01L 7/52 |
| | | | | 435/286.1 |

(Continued)

FOREIGN PATENT DOCUMENTS

| | | |
|---|---|---|
| CN | 103525697 A | 1/2014 |
| CN | 105358673 A | 2/2016 |

(Continued)

*Primary Examiner* — Matthew D Krcha

(57) ABSTRACT

A molecular diagnostics apparatus is provided. The molecular diagnostics apparatus is adapted to perform DNA chain replication to one sample. The molecular diagnostics apparatus includes a bracket, a central control module, a motor, a magnetic unit, a rotational carrier, a detection module and at least one power supply coil. The central control module is disposed on the bracket. The motor is disposed on the bracket, wherein the central control module drives the motor. The magnetic unit is disposed on the bracket, wherein the magnetic unit provides a magnetic field. The motor is adapted to rotate the rotational carrier. The rotational carrier is rotated relative to the bracket. The sample is disposed on the rotational carrier. The detection module is disposed on the rotational carrier. The power supply coil is coupled to the detection module, and disposed on the rotational carrier. The molecular diagnostics apparatus of the embodiment has a simpler structure and better reliability.

20 Claims, 16 Drawing Sheets

(56) References Cited

U.S. PATENT DOCUMENTS

2013/0157276 A1\* 6/2013 Edvinsson ................ B01L 7/52
                                                  435/6.12
2013/0224744 A1  8/2013 Renna et al.
2016/0136647 A1\* 5/2016 Sung ......................... B01L 7/52
                                                  435/286.1

FOREIGN PATENT DOCUMENTS

| TW | M393516 U1 | 12/2010 |
| TW | 201617600 A | 5/2016 |
| TW | I591174 B | 7/2017 |

\* cited by examiner

MOLECULAR DIAGNOSTICS APPARATUS

CROSS REFERENCE TO RELATED APPLICATIONS

This application claims priority of Taiwan Patent Application No. 108216368, filed on Dec. 10, 2019, the entirety of which is incorporated by reference herein.

BACKGROUND OF THE INVENTION

Field of the Invention

The present invention relates to a molecular diagnostics apparatus, and in particular to a molecular diagnostics apparatus with a wireless power supply.

Description of the Related Art

Polymerase chain reaction (PCR) is a method widely used in molecular biology to rapidly make millions to billions of copies of a specific DNA sample allowing scientists to take a very small sample of DNA and amplify it to a large enough amount to study in detail. Real-Time PCR (quantitative-PCR, q-PCR) can monitor the entire polymerase chain reaction in real time. The polymerase chain reaction mainly includes a temperature control part and a detection part. The temperature control part provides the temperature cycling required for the polymerase chain reaction. The detection part uses a specific excitation wavelength to make the fluorescence dye emit a fluorescence signal. An optical sensor and a filter are then utilized to capture and detect a specific wavelength band. Performing a polymerase chain reaction once can get about 2 times the DNA amplified products. After performing N times, about $2^N$ DNA amplified products can be obtained. When the DNA amplified product doubles, the fluorescence signal gradually increases and accumulates. Therefore, real-time PCR (q-PCR) can be used to monitor the temperature and fluorescence changes of the entire polymerase chain reaction in real time, to record the number of cycles and fluorescence intensity changes, and to quantitatively analyze the DNA concentration.

Conventionally, the molecular diagnostics apparatus has a rotational carrier and a temperature detection module. The temperature detection module is disposed on the rotational carrier. The temperature data provided by the temperature detection module and the required power are transmitted by a signal-cable and a power-cable. One end of the signal-cable/power-cable is connected to a fixed central control module, and the other end of the signal-cable/power-cable is connected to the rotating temperature detection module. Therefore, the reliability of the signal-cable/power-cable is low, and the overall mechanism design of the molecular diagnostics apparatus is complicated.

BRIEF SUMMARY OF THE INVENTION

Embodiments of the inventions are provided to solve the aforementioned difficulty.

In one embodiment, a molecular diagnostics apparatus is provided. The molecular diagnostics apparatus is adapted to perform DNA chain replication to one sample. The molecular diagnostics apparatus includes a bracket, a central control module, a motor, a magnetic unit, a rotational carrier, a detection module and at least one power supply coil. The central control module is disposed on the bracket. The motor is disposed on the bracket. The central control module drives the motor. The magnetic unit is disposed on the bracket. The magnetic unit provides a magnetic field. The motor is adapted to rotate the rotational carrier. The rotational carrier is rotated relative to the bracket. The sample is disposed on the rotational carrier. The detection module is disposed on the rotational carrier. The power supply coils are coupled to the detection module, and disposed on the rotational carrier. In a charging mode, the central control module drives the motor to rotate the rotational carrier, the power supply coil generates a first induced current according to the magnetic field, and the first induced current is supplied to the detection module.

In another embodiment, a molecular diagnostics method is provided. The molecular diagnostics method is adapted to perform DNA chain replication to one sample. The molecular diagnostics method includes the following steps. First, a molecular diagnostics apparatus is provided. The molecular diagnostics apparatus comprises a bracket, a central control module, a motor, a magnetic unit, a rotational carrier, a detection module and at least one power supply coil, the central control module is disposed on the bracket, the motor is disposed on the bracket, the central control module drives the motor, the magnetic unit is disposed on the bracket, the magnetic unit provides a magnetic field, the motor is adapted to rotate the rotational carrier, the rotational carrier is rotated relative to the bracket, the sample is disposed on the rotational carrier, the detection module is disposed on the rotational carrier, the power supply coils are coupled to the detection module and disposed on the rotational carrier. Then, an optical system of the molecular diagnostics apparatus is provided, the optical system is affixed to the bracket, and the power supply coils are surrounding the optical system. Next, a temperature control module of the molecular diagnostics apparatus is provided, the temperature control module is adapted to control the temperature of the rotational carrier, the detection module comprises a temperature detection module, the detection module detects the temperature of the rotational carrier and generates temperature data. In a charging mode, the central control module drives the motor to rotate the rotational carrier, the power supply coil generates a first induced current according to the magnetic field, and the first induced current is supplied to the detection module.

Utilizing the molecular diagnostics apparatus of the embodiment of the invention, the detection module is charged by principle of magnetic field induction. The conventional signal cable and power cable are omitted. The structure of the molecular diagnostics apparatus is simplified. The reliability of the signal transmission and power transmission can be improved.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1A:
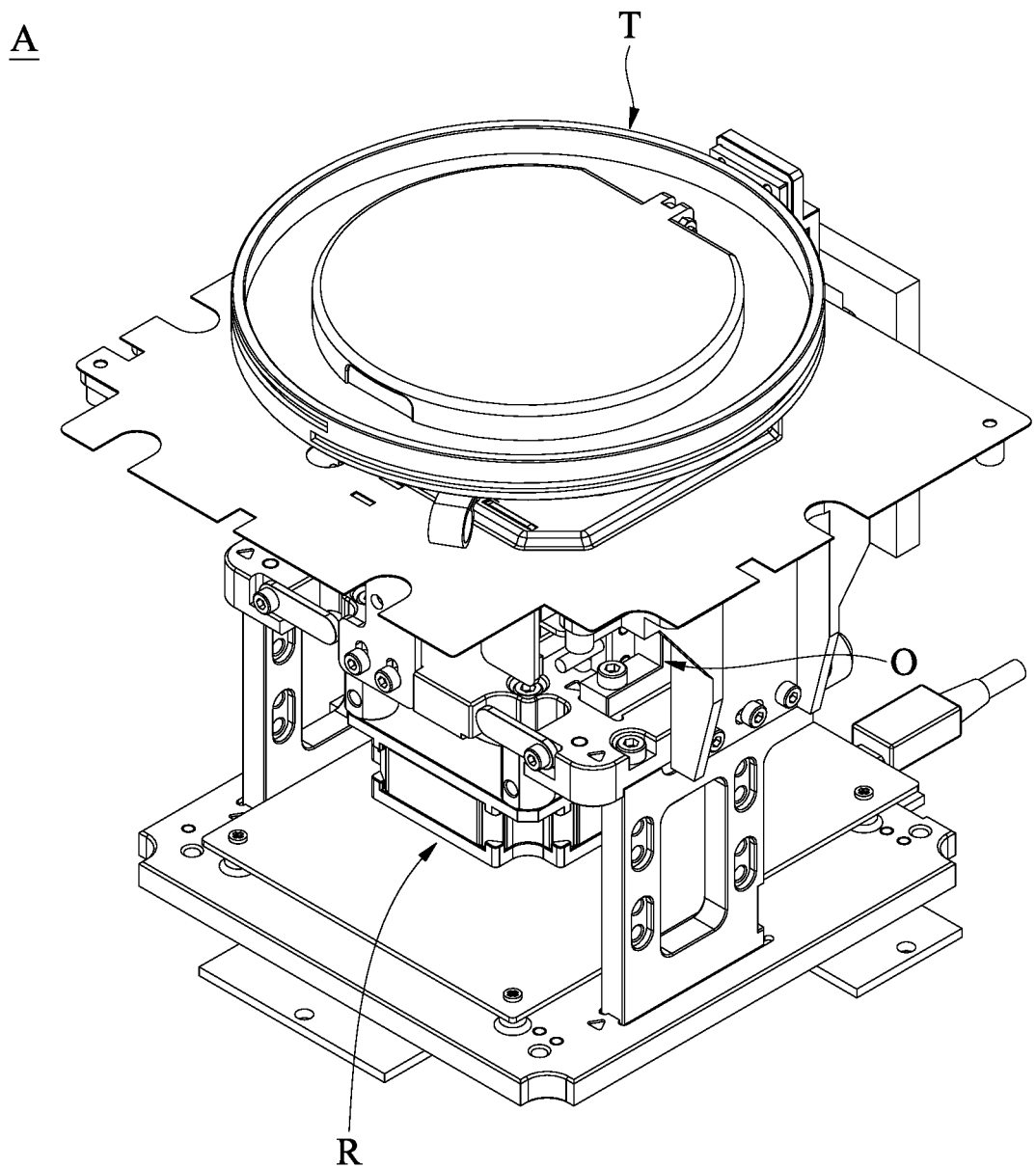
FIG. 1A is an assembled view of a molecular diagnostics apparatus of the embodiment of the invention.
Figure 1B:
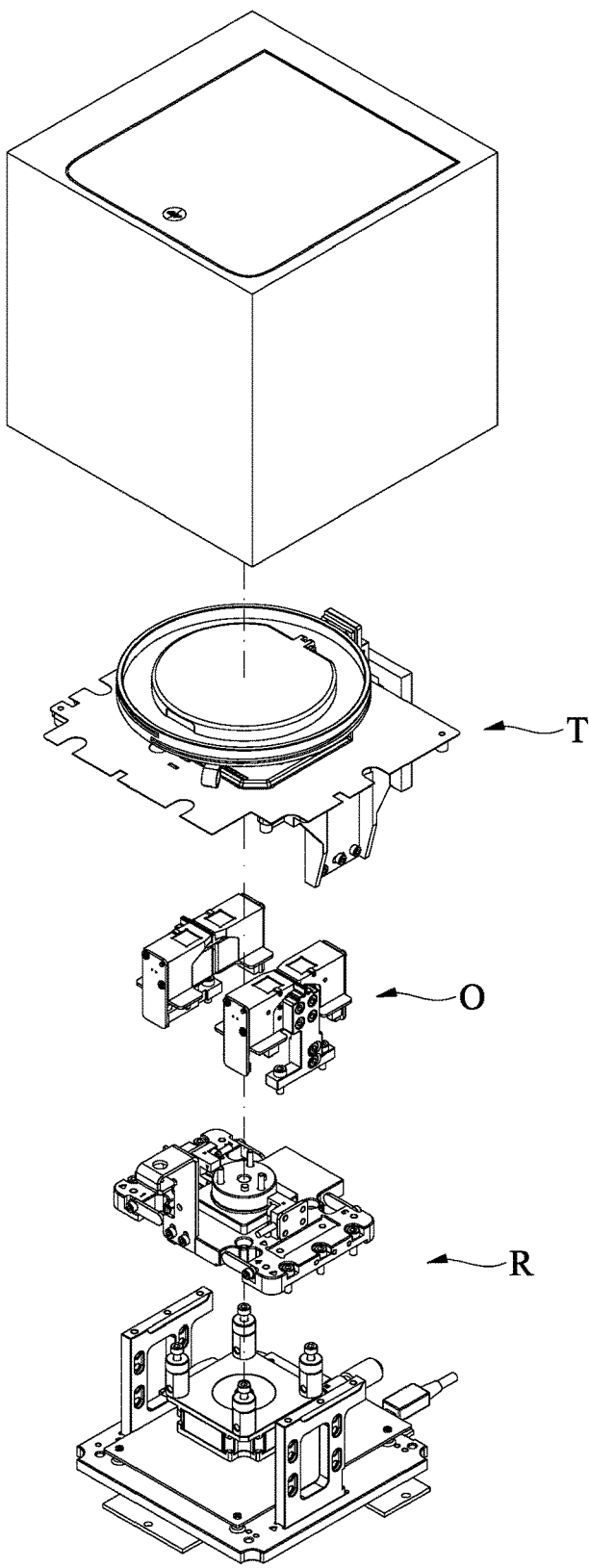
FIG. 1B is an exploded view of the molecular diagnostics apparatus of the embodiment of the invention.

FIG. 1A is an assembled view of a molecular diagnostics apparatus of the embodiment of the invention. FIG. 1B is an exploded view of the molecular diagnostics apparatus of the embodiment of the invention. With reference to FIGS. 1A and 1B, in one embodiment, the molecular diagnostics apparatus A of the embodiment of the invention is a real-time polymerase chain reaction (qPCR) apparatus. The molecular diagnostics apparatus A includes a temperature control system T, an optical system O and a rotation system R. The temperature control system T provides the three-stage temperature cycle required for the polymerase chain reaction thermal cycle to the test tube containing the fluorescence dye. The process of polymerase chain reaction must include a denaturation step whose temperature is raised to 94° C., an annealing step whose temperature is decreased to 50° C.~60° C., and an extension step whose temperature is raised to 72° C. The optical system O captures data and analyzes the fluorescence signal excited by the fluorescence dye in the test tube after each thermal cycle. The rotation system R utilizes a motor to rotate the turntable of the temperature control system (in one embodiment, the turntable carries sixteen test tubes). Therefore, the sixteen test tubes containing fluorescence dye can correspond to different optical system positions. The specific excitation wavelength of the optical system O causes the fluorescence dye to generate a fluorescent signal. Then, a photodiode of the optical system O captures the fluorescence brightness and analyzes the final DNA concentration. The above temperature values can be adjusted according to different DNA sequence and different reagents/dyes.

Figure 2A:
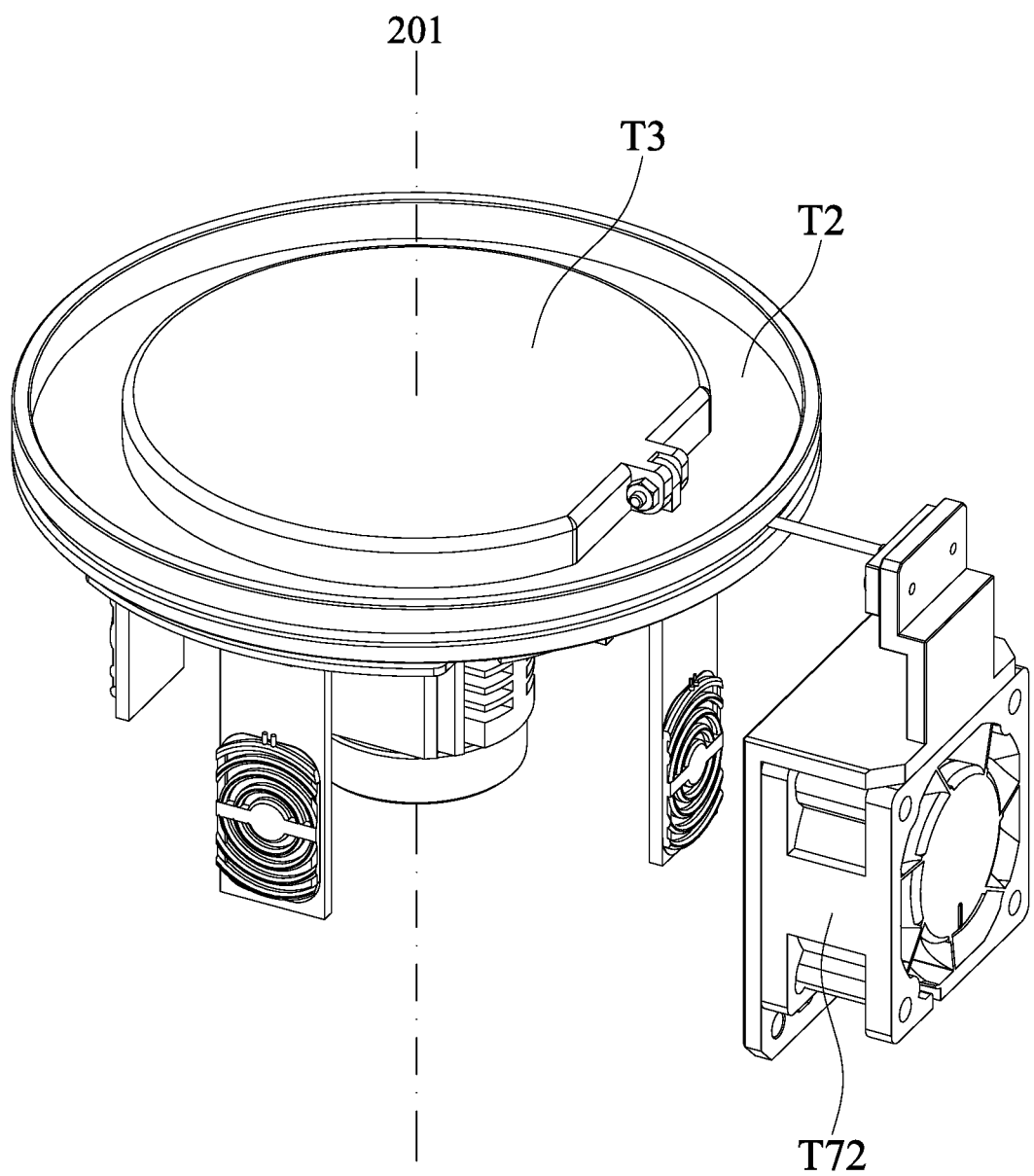
FIGS. 2A and 2B show details of a temperature control system of the embodiment of the invention.
Figure 2B:
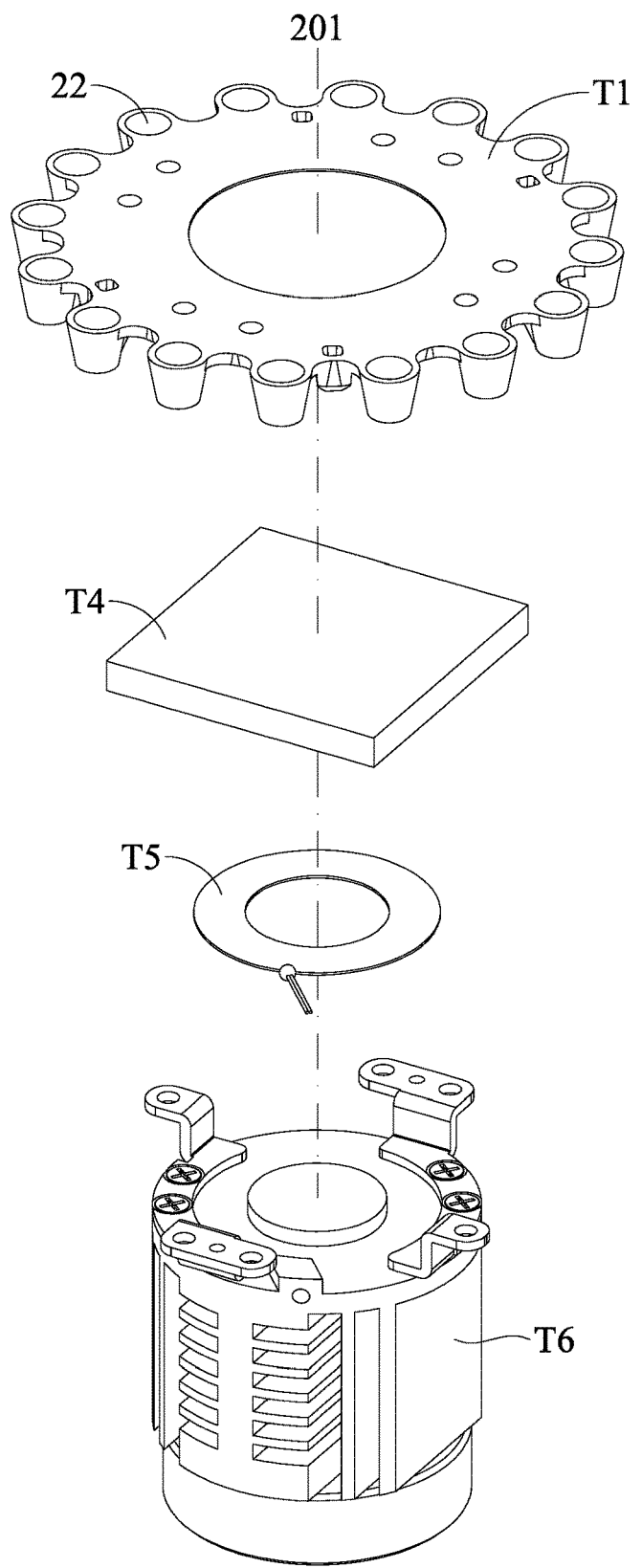
Figure 2C:
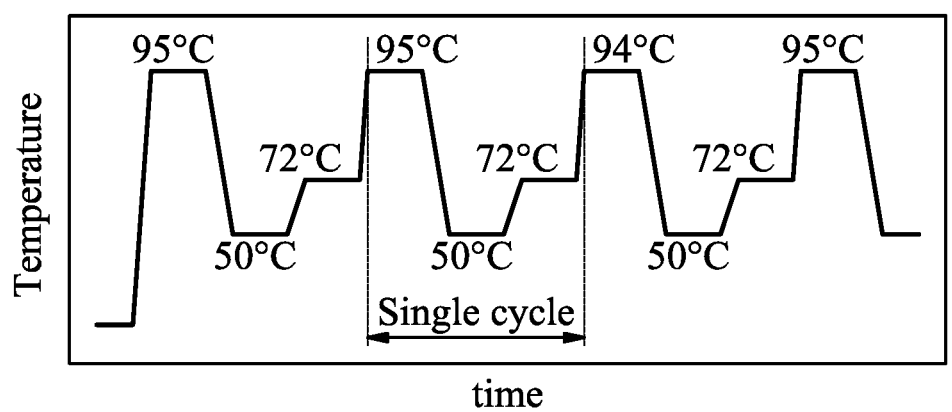
FIG. 2C shows the temperature of the three-stage temperature cycle required for the polymerase chain reaction of the embodiment of the invention.

FIGS. 2A and 2B show details of the temperature control system of the embodiment of the invention. With reference to FIGS. 2A and 2B, the temperature control system T of the embodiment of the invention utilizes a thermoelectric cooling chip (TEC) for heating and cooling to make the temperature rise and fall rapidly. The temperature control system T includes a heating block T1, a holder T2, a cover T3, a thermoelectric cooling chip T4, a heater T5, a heat sink T6, a fan duct T71 and a fan T72. Heating block T1 is used to place the test tube. The holder T2 is used to prevent the test tube from tilting. The cover T3 is used to apply pressure to bring the test tube into contact with the heating block T1. The thermoelectric cooling chip (TEC) T4 is used to precisely adjust the temperature rise and fall with the heater T5, the heat sink T6, the fan duct T71 and the fan T72. The temperature of the three-stage temperature cycle required for the polymerase chain reaction is shown in FIG. 2C. At the beginning, the denaturation step is performed, and the temperature is increased to the first stage temperature of 94° C. The hot end of the thermoelectric cooling chip T4 contacts the heating block T1 to raise the temperature of the heating block T1. At this time, the heater T5 is turned on and heats the heating block T1 with the thermoelectric cooling chip T4. A computer program is used to control and maintain the temperature of the first stage of the polymerase chain reaction. Another function of the heater T5 is to maintain the temperature difference between the two ends of the thermoelectric cooling chip T4 at a certain value, so as to maintain the heating rate. Then, the annealing step is performed, and the temperature is decreased to the second stage temperature of 55° C.~60° C. At this time, the voltage applied to the thermoelectric cooling chip T4 is reversed, and the cold and hot ends are switched. The heater T5 is turned off and the fan T72 is turned on. The heat sink T6 conducts the heat from the hot end of the thermoelectric cooling chip T4. The fan T72 forces convection to export the heat outside the apparatus and adjust the temperature precisely with the temperature difference between the two ends of the thermoelectric cooling chip T4. Finally, the extension step is performed, and the temperature is raised to the third stage temperature of 72° C.

Figure 3:
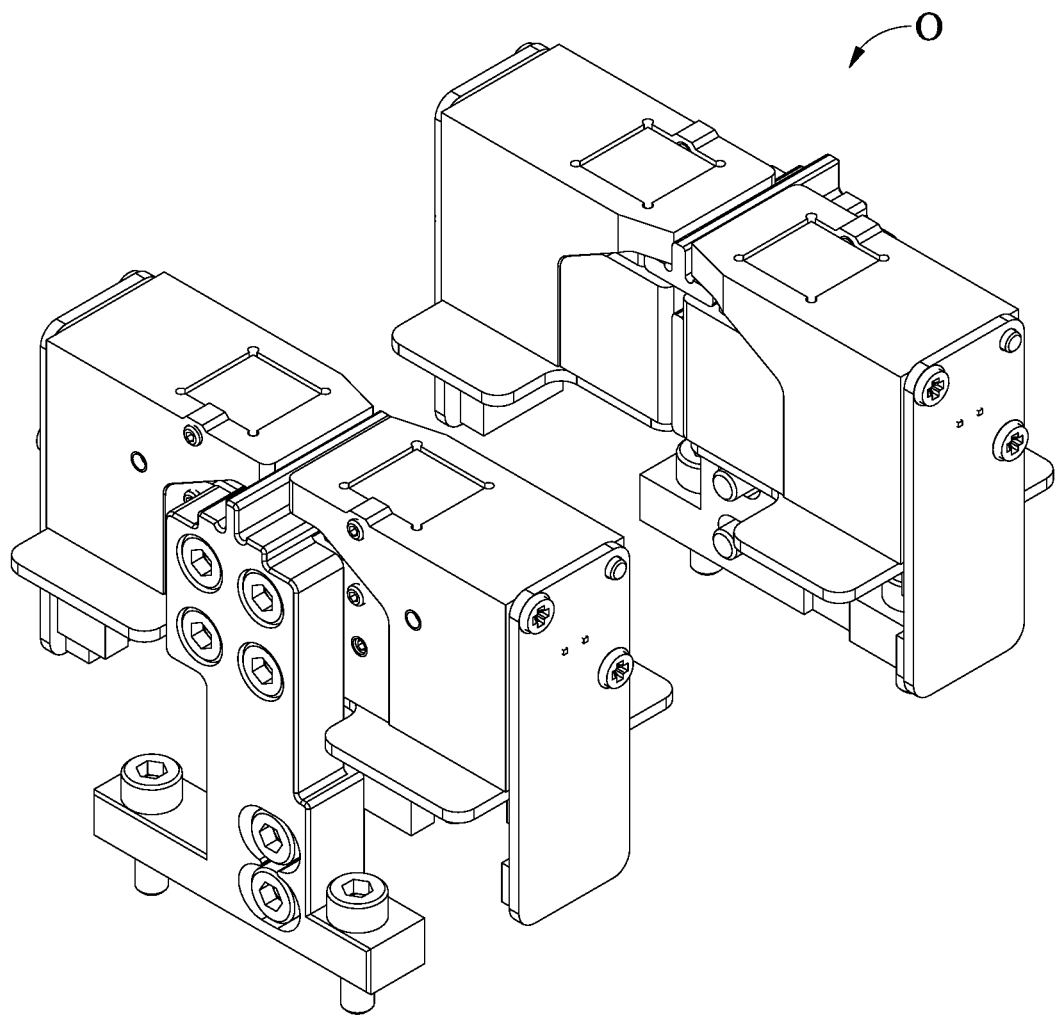
FIG. 3 shows details of an optical system of the embodiment of the invention.

FIG. 3 shows details of the optical system of the embodiment of the invention. With reference to FIG. 3, in one embodiment of the invention, the optical system O has four optical devices. Each optical device includes an excitation filter, a dichroic filter, an emission filter, and a photodiode. In one embodiment, the aforementioned optical device can be used to detect four kinds of specific fluorescence dyes: green (excitation peak at 494 nm, emission peak at 520 nm), yellow (excitation peak at 550 nm, emission peak at 570 nm), orange (excitation peak at 575 nm, emission peak at 602 nm), and red (excitation peak at 646 nm, emission peak at 662 nm).

As to the details of the optical device, in the optical device, the light emitted by the monochromatic light-emitting diode (LED) passes through the excitation filter, and is reflected by the dichroic filter (the dichroic filter can reflect the short wave and allow the long wave to pass), and shines upward toward the bottom of the test tube containing the fluorescence dye. After the fluorescence dye is excited, the fluorescent light passes through the dichroic filter and the emission filter. After filtering out all unwanted noise light sources, it is received by a photodiode. After a series of light paths, the final change in fluorescence characteristics is observed for analysis.

Figure 4:
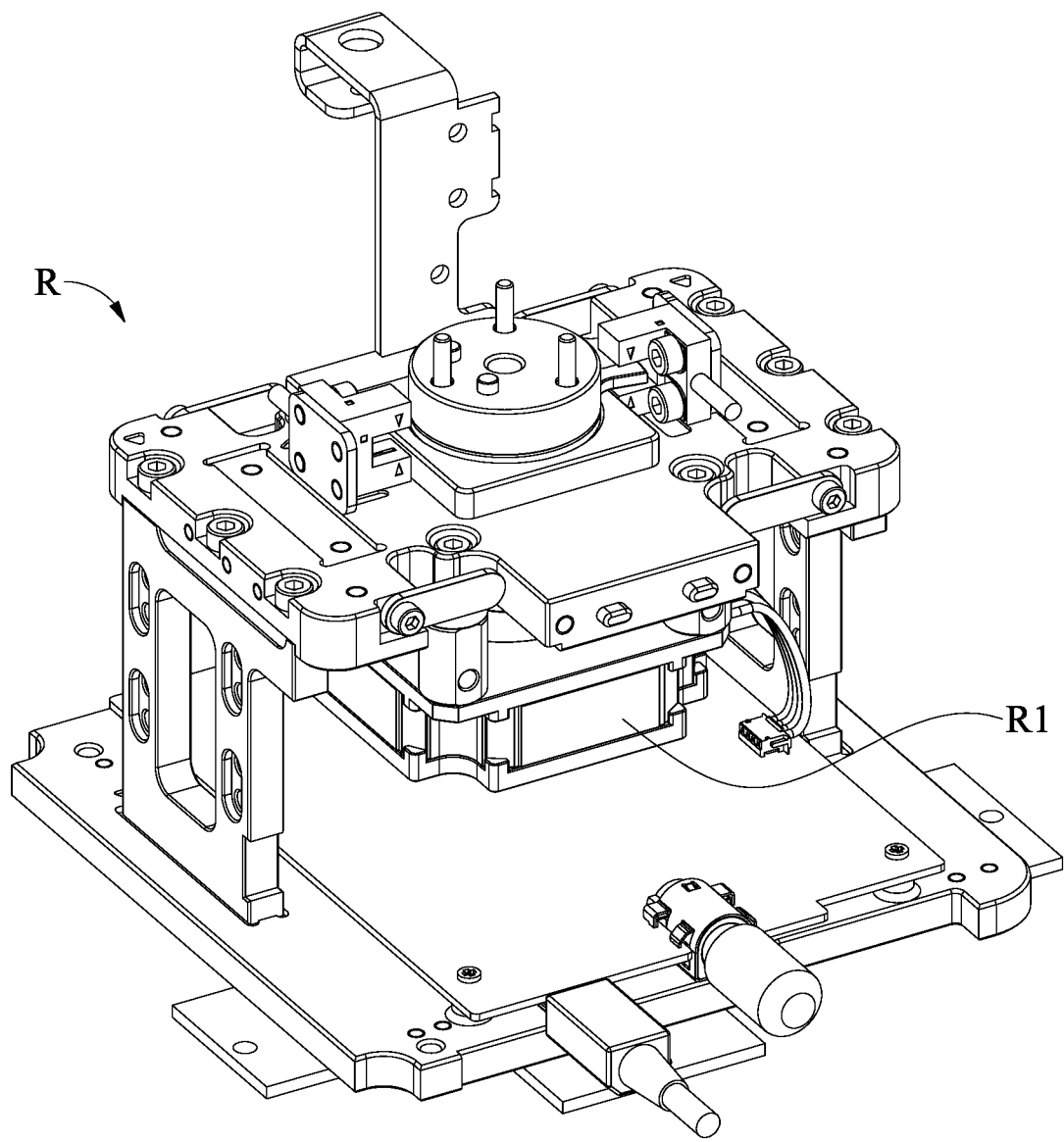
FIG. 4 shows a rotation system of the embodiment of the invention.

FIG. 4 shows the rotation system of the embodiment of the invention. With reference to FIG. 4, the motor R1 of the rotation system R directly rotates the temperature control system T, so that the test tubes containing the fluorescence dye on the temperature control system T can correspond to the positions of the four optical devices for being detected. In an embodiment, the rotation system R may include a limit sensor, which detects the initial point (Home) and the stopping point (End) in the rotation position of the motor R1 by using a light interruption method. The molecular diagnostics apparatus differentiates the test tube through the collaboration of the firmware and the software.

Figure 5A:
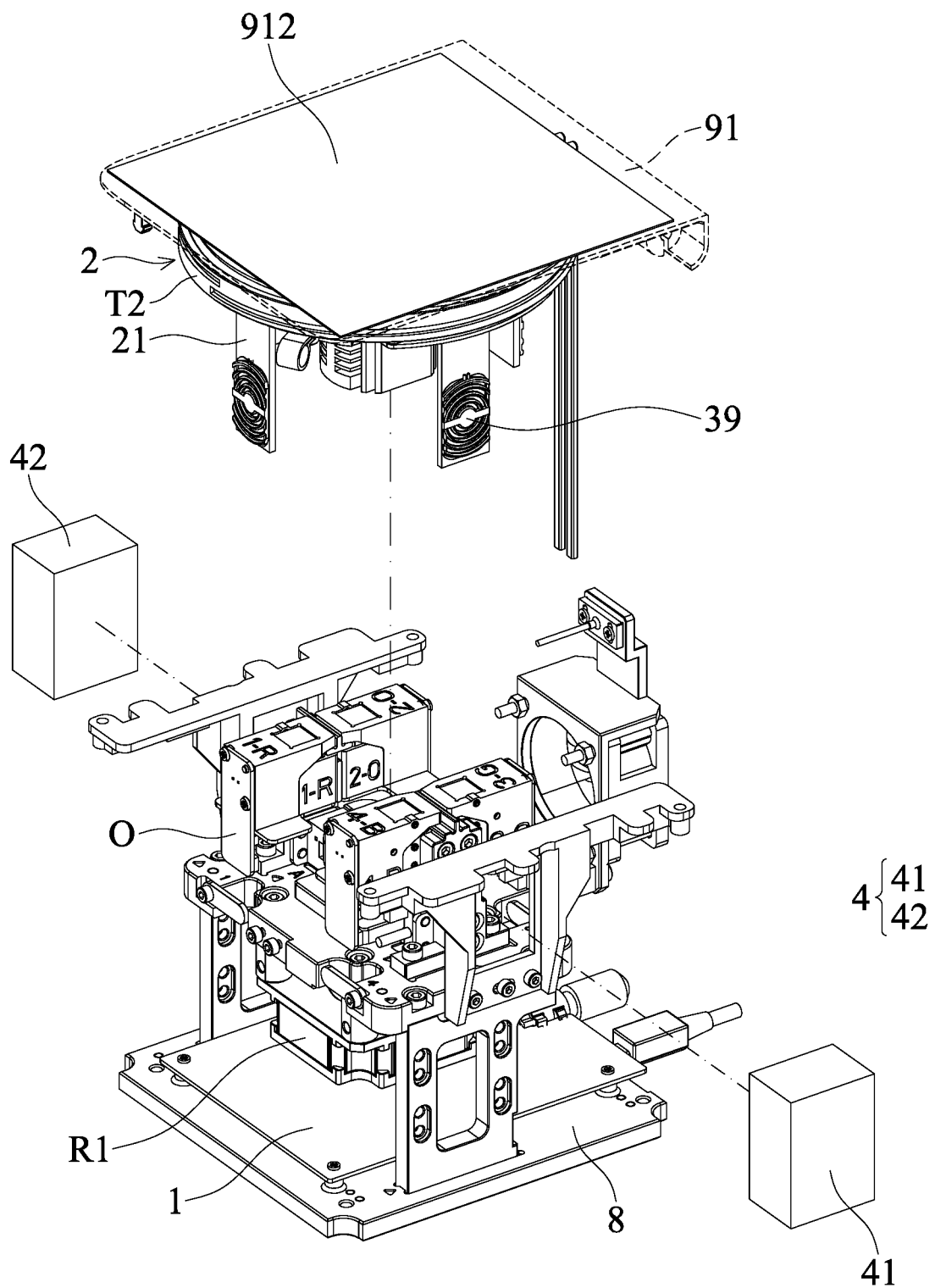
FIG. 5A is a perspective view of a molecular diagnostics apparatus of the embodiment of the invention.
Figure 5B:
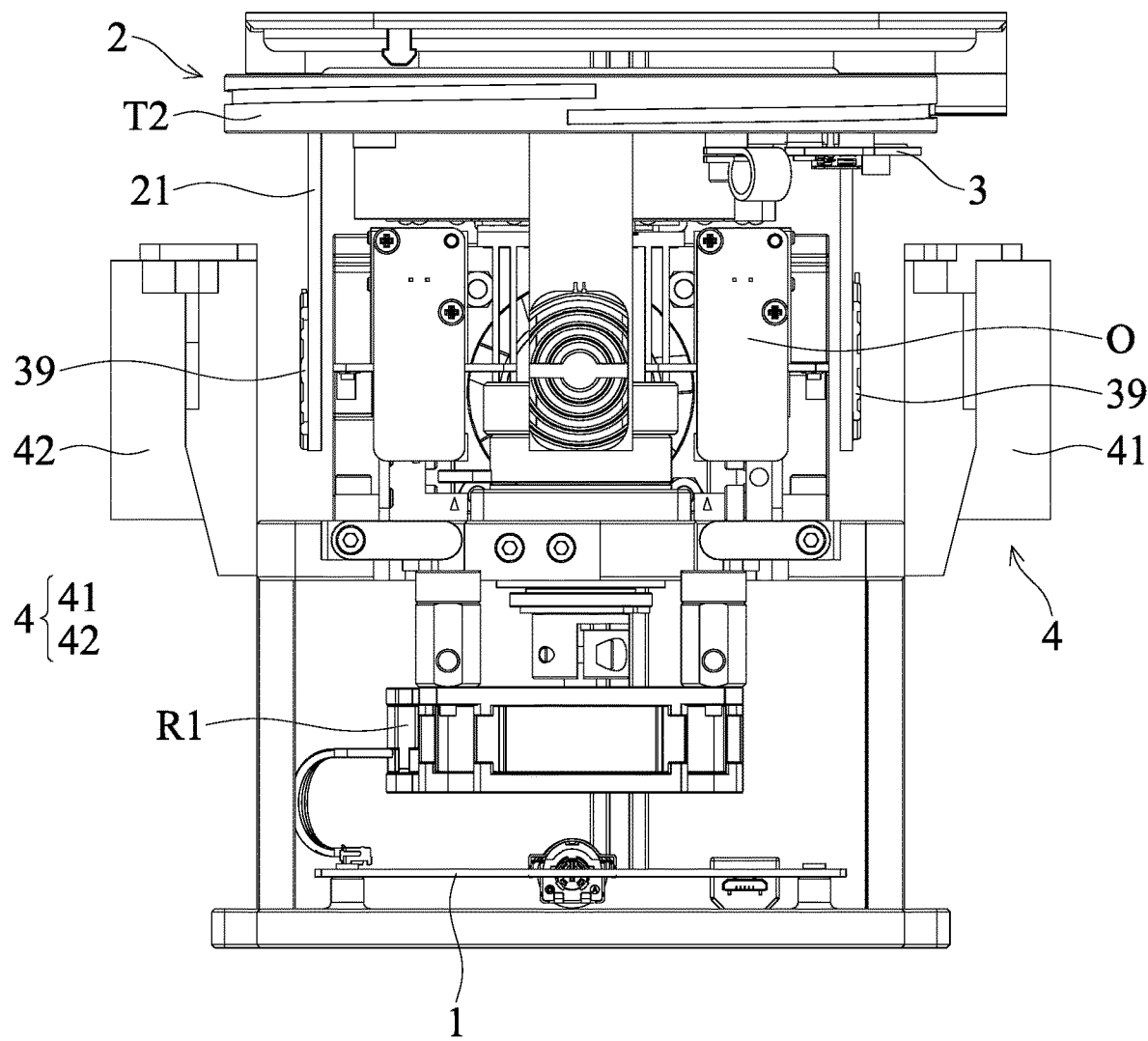
FIG. 5B shows a detection module and a detection module coil of the embodiment of the invention.

FIG. 5A is a perspective view of a molecular diagnostics apparatus of the embodiment of the invention. FIG. 5B shows a detection module and a detection module coil of the embodiment of the invention. With reference to FIGS. 5A and 5B, in one embodiment, the molecular diagnostics apparatus is adapted to perform DNA chain replication to one sample. The molecular diagnostics apparatus includes a bracket 8, a central control module 1, a motor R1, a magnetic unit 4, a rotational carrier 2, a detection module 3 and at least one power supply coil 39. The central control module 1 is disposed on the bracket 8. The motor R1 is disposed on the bracket 8. The central control module 1 drives the motor R1. The magnetic unit 4 is disposed on the bracket 8. The magnetic unit 4 provides a magnetic field. The motor R1 is adapted to rotate the rotational carrier 2. The rotational carrier 2 is rotated relative to the bracket 8. The sample is disposed on the rotational carrier 2. The detection module 3 is disposed on the rotational carrier 2. The power supply coil 39 are coupled to the detection module 3, and disposed on the rotational carrier 2. In a charging mode, the central control module 1 drives the motor R1 to rotate the rotational carrier 2, the power supply coil 39 generates a first induced current according to the magnetic field, and the first induced current is supplied to the detection module 3.

With reference to FIGS. 2A and 2B, in one embodiment, the rotational carrier 2 includes said heating block T1, said holder T2 and said cover T3. With reference to FIGS. 5A and 5B, in one embodiment, the rotational carrier 2 further comprises the holder T2 and at least one coil mounting member 21. The detection module 3 is disposed on the holder T2. The power supply coil 39 is disposed on a coil mounting member 21. The coil mounting member 21 is connected to the holder T2.

Figure 5C:
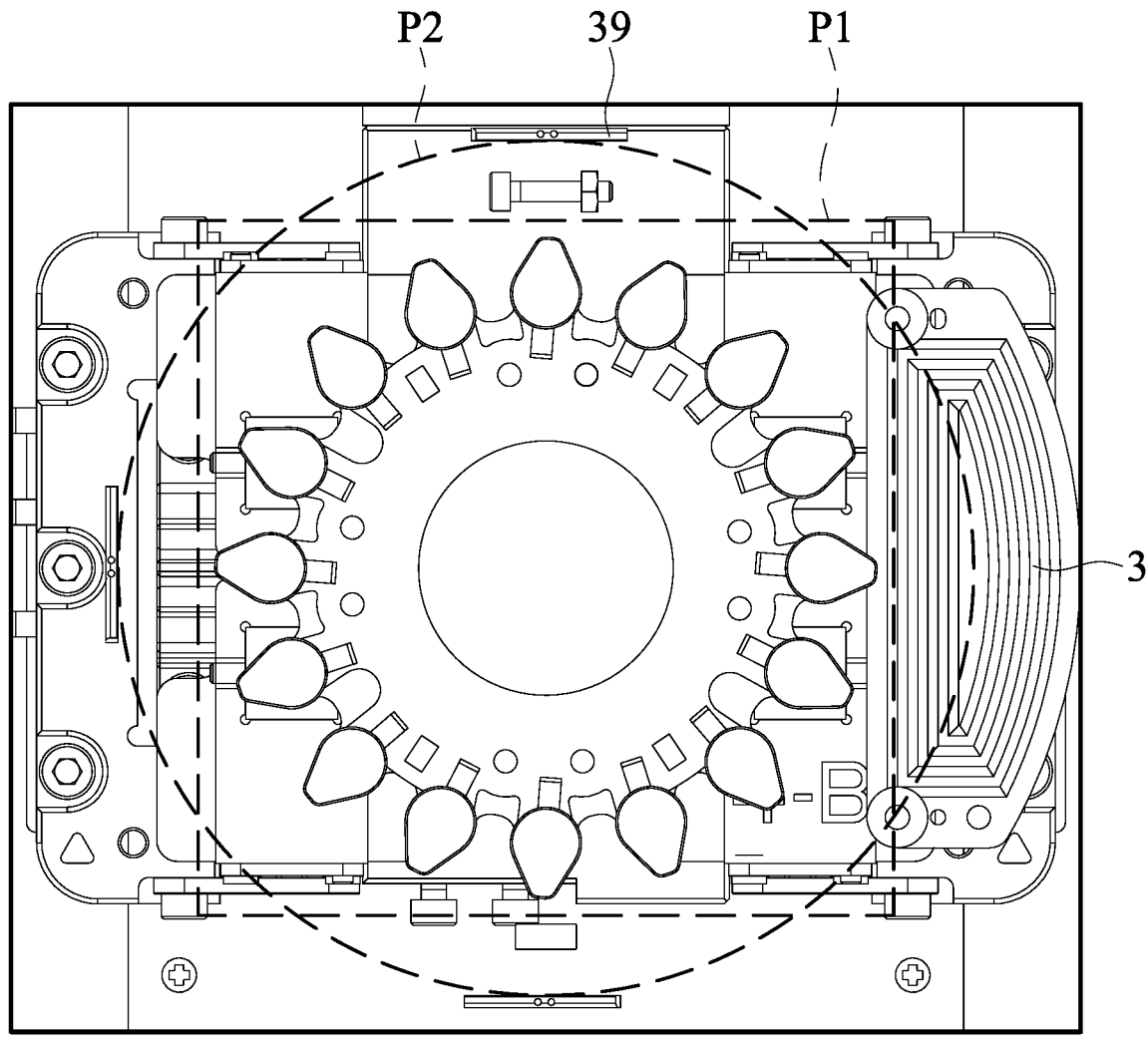
FIG. 5C is a top view of the molecular diagnostics apparatus of the embodiment of the invention.

FIG. 5C is a top view of the molecular diagnostics apparatus of the embodiment of the invention. With reference to FIGS. 5B and 5C, in one embodiment, the holder T2 is on a virtual flat plane P1, the coil mounting member 21 is on a virtual curved plane P2, and the virtual curved plane P2 is orthogonal to the virtual flat plane P1.

With reference to FIGS. 5A and 5B, in one embodiment, the molecular diagnostics apparatus further comprises said optical system O. The optical system O is affixed to the bracket 8, and the power supply coils 39 surround the optical system O. Therefore, the power supply coils 39 can be avoided from being interfered with the optical system O.

With reference to FIGS. 5A and 5B, in one embodiment, the magnetic unit 4 comprises an N-pole magnet 41 and an S-pole magnet 42. The optical system O and the power supply coils 39 are located between the N-pole magnet 41 and the S-pole magnet 42.

With reference to FIGS. 2A and 2B, in one embodiment, the molecular diagnostics apparatus further comprises a temperature control module (including said thermoelectric cooling chip T4, said heater T5, said heat sink T6 and said fan T72). The temperature control module is adapted to control a temperature (rise and fall) of the rotational carrier. The detection module 3 is a temperature detection module.

The detection module 3 detects the temperature of the rotational carrier 2 and generates temperature data.

With reference to FIGS. 2A and 2B, in one embodiment, the rotational carrier 2 comprises a plurality of receiving recesses 22 (disposed on the heating block T1). The receiving recesses 22 are arranged annularly around an axis 201 of the rotational carrier 2. The sample is adapted to be disposed in one of the receiving recesses 22.

With reference to FIGS. 5A and 5B, in one embodiment, the molecular diagnostics apparatus further comprising an upper cover 91 and an upper cover display module 912. The upper cover display module 912 is disposed on the upper cover 91. The detection module 3 comprises a detection module coil (not shown). The upper cover display module 912 comprises a display module coil (not shown). The detection module coil provides an induced electromotive force (electromagnetic field). The display module coil generates a second induced current according to the induced electromotive force (electromagnetic field). The second induced current is supplied to the upper cover display module 912. Therefore, the upper cover display module 912 can show some information such as the progress of the molecular diagnostics process. In one embodiment, the detection module coil transfers electric power to the display module coil through magnetic induction. In another embodiment, the detection module coil transfers electric power to the display module coil through magnetic resonance. A resonant frequency of the detection module coil and its matching circuit is the same as a resonant frequency of the display module coil and its matching circuit. In another embodiment, an induction frequency of the coil can be enhanced to improve the electromotive force (electromagnetic field).

Figure 6A:
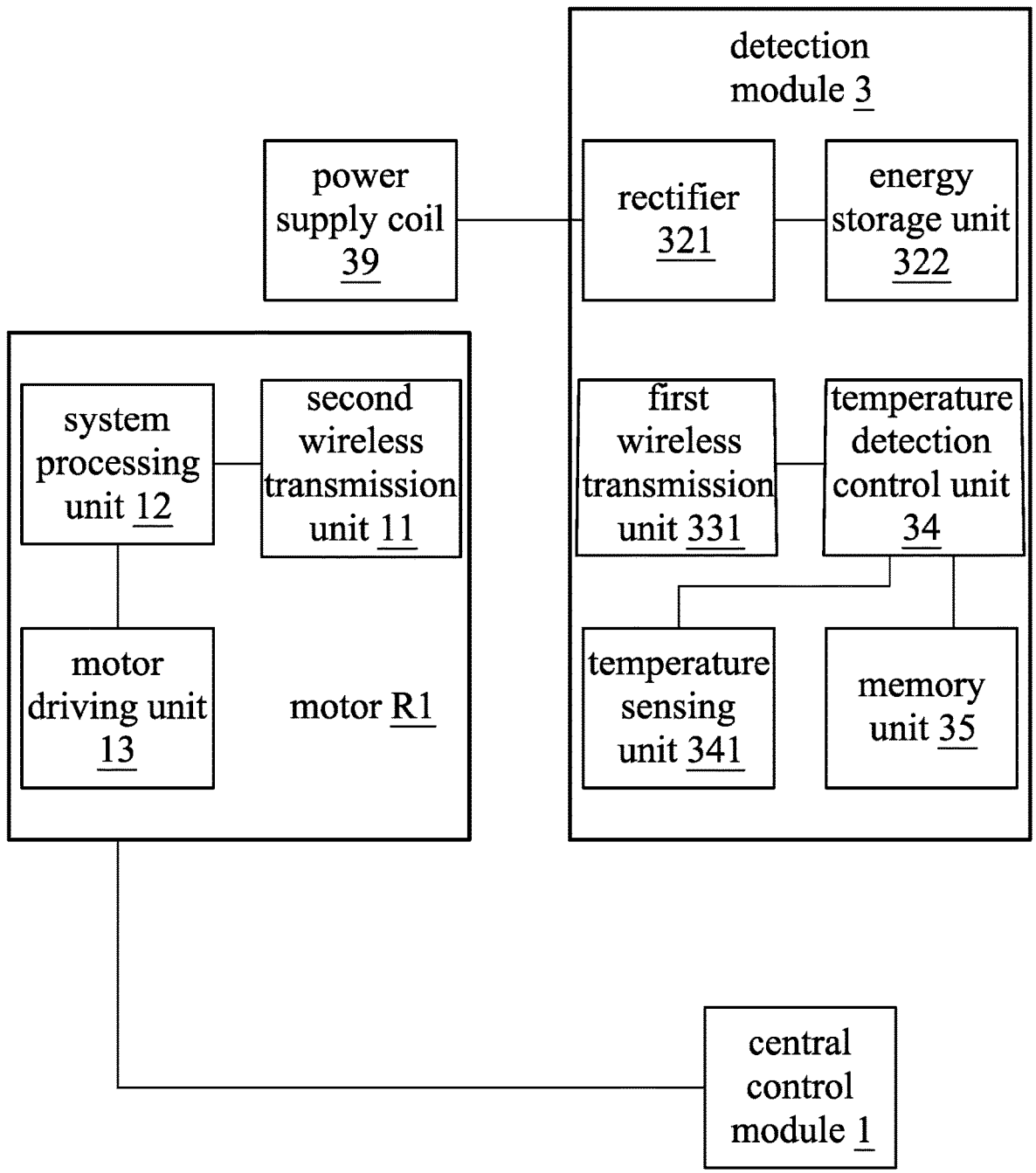
FIG. 6A is a block diagram of a molecular diagnostics apparatus of the embodiment of the invention.

FIG. 6A is a block diagram of a molecular diagnostics apparatus of the embodiment of the invention. With reference to FIG. 6A, in one embodiment, the detection module 3 comprises a rectifier 321, an energy storage unit 322, a first wireless transmission unit 331, a temperature detection control unit 34 and a temperature sensing unit 341. The rectifier 321 is coupled to the power supply coil 39 and the energy storage unit 322. The temperature detection control unit 34 is coupled to the temperature sensing unit 341 and the first wireless transmission unit 331. The central control module 1 comprises a second wireless transmission unit 11, a system processing unit 12 and a motor driving unit 13. The system processing unit 12 is coupled to the second wireless transmission unit 11 and the motor driving unit 13. In one embodiment, the system processing unit 12 including a Memory Control Unit (MCU).

Figure 6B:
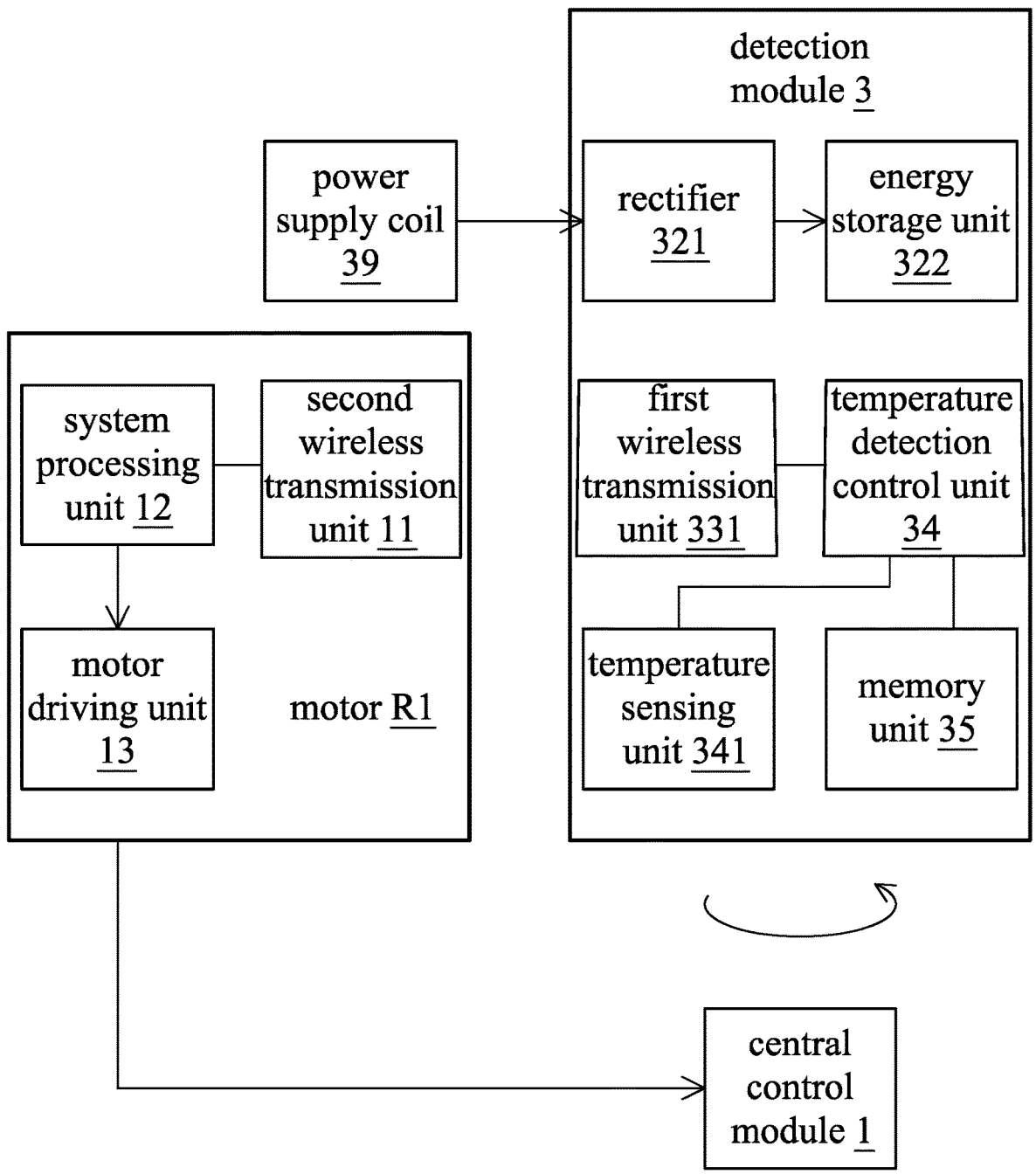
FIG. 6B is a block diagram of a molecular diagnostics apparatus of the embodiment of the invention, wherein the molecular diagnostics apparatus is in a charging mode.

FIG. 6B is a block diagram of the molecular diagnostics apparatus of the embodiment of the invention, wherein the molecular diagnostics apparatus is in a charging mode. With reference to FIG. 6B, in the charging mode, the system processing unit 12 controls the motor R1 via the motor driving unit 13. The motor R1 rotates the rotational carrier 2. The power supply coils 39 between the N-pole magnet 41 and the S-pole magnet 42 are rotated with the rotational carrier 2. The power supply coils 39 therefore generate the first induced current according to the magnetic field. The first induced current passes through the rectifier 321 and charges the energy storage unit 322. The energy storage unit 322 provides power to the detection module 3.

Figure 6C:
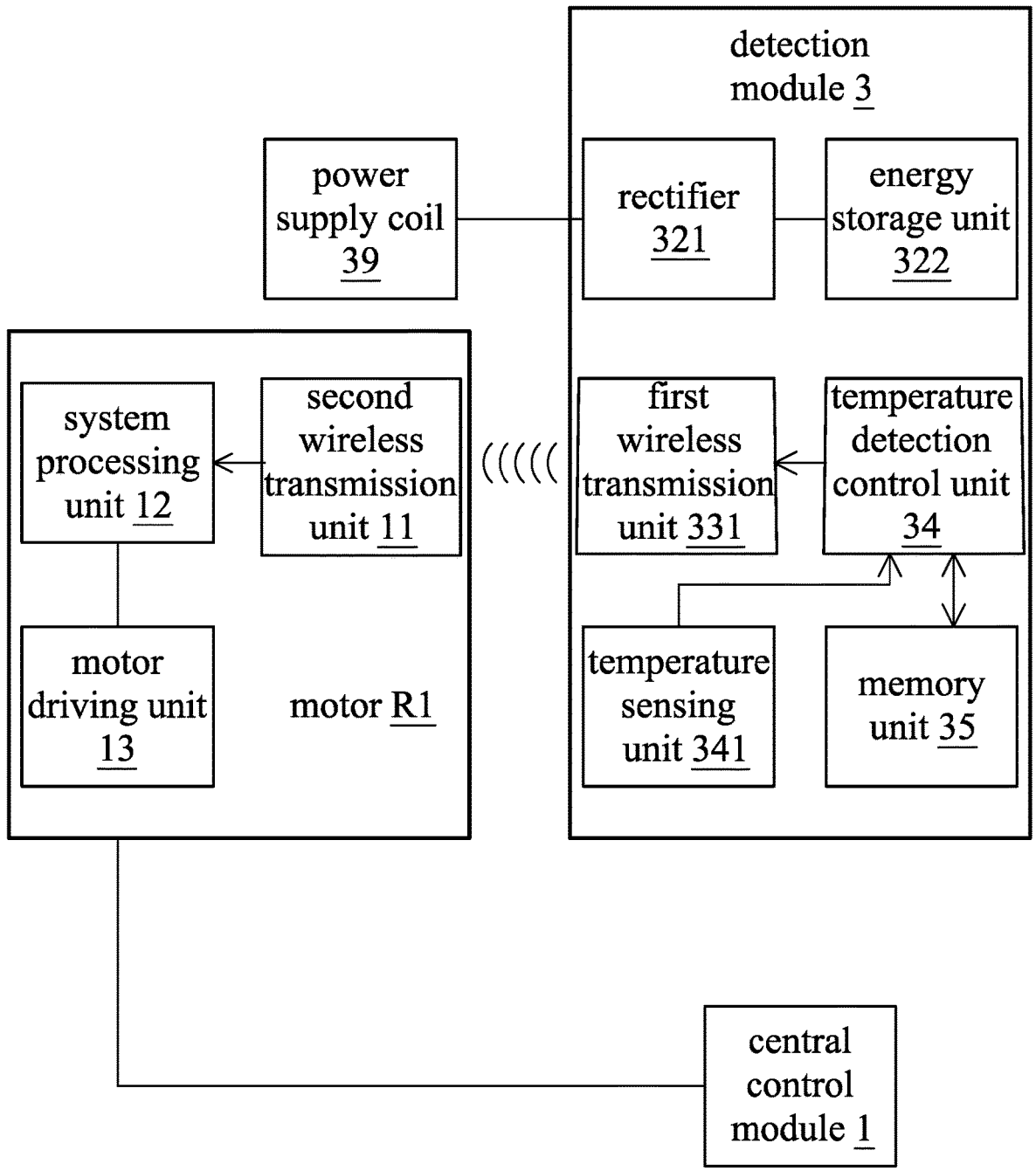
FIG. 6C is a block diagram of a molecular diagnostics apparatus of the embodiment of the invention, wherein the molecular diagnostics apparatus is in a feedback mode.

FIG. 6C is a block diagram of the molecular diagnostics apparatus of the embodiment of the invention, wherein the molecular diagnostics apparatus is in a feedback mode. With reference to FIG. 6C, in the feedback mode, the temperature sensing unit 341 detects the temperature of the rotational carrier 2 and generates temperature data. The temperature detection control unit 34 sends the temperature data to the first wireless transmission unit 331. The first wireless transmission unit 331 sends the temperature data. The second transmission unit 11 receives the temperature data sent from the first wireless transmission unit 331. The temperature data is transmitted to the system processing unit 12.

With reference to FIG. 6C, in one embodiment, the detection module 3 further comprises a memory unit 35. The temperature data is stored in the memory unit 35. The temperature detection control unit 34 reads the temperature data from the memory unit 35 and sends the temperature data to the first wireless transmission unit 331.

In the embodiment of the invention, the first wireless transmission unit 331 can communicate with the second wireless transmission unit 11 via Bluetooth or other communication specifications. The disclosure is not meant to restrict the invention.

Figure 7A:
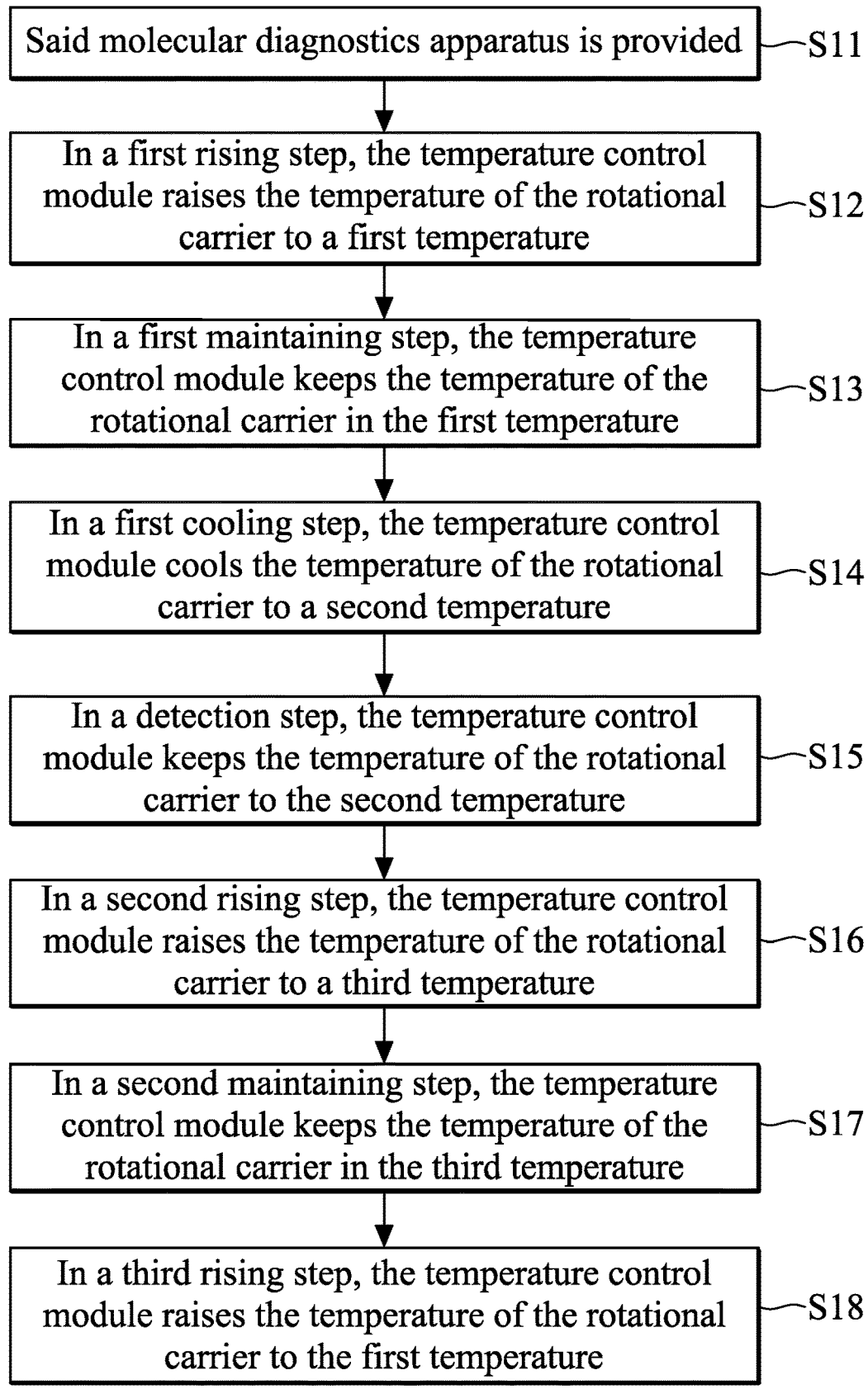
FIG. 7A shows a molecular diagnostics method of the embodiment of the invention.

FIG. 7A shows a molecular diagnostics method of the embodiment of the invention. The molecular diagnostics method is adapted to perform DNA chain replication to one sample. The molecular diagnostics method includes the following steps. First, said molecular diagnostics apparatus is provided (S11). Then, in a first rising step, the temperature control module raises the temperature of the rotational carrier 2 to a first temperature (S12). Then, in a first maintaining step, the temperature control module keeps the temperature of the rotational carrier 2 in the first temperature (S13). Next, in a first cooling step, the temperature control module cools the temperature of the rotational carrier 2 to a second temperature (S14). Then, in a detection step, the temperature control module keeps the temperature of the rotational carrier 2 to the second temperature (S15). Next, in a second rising step, the temperature control module raises the temperature of the rotational carrier 2 to a third temperature (S16). Then, in a second maintaining step, the temperature control module keeps the temperature of the rotational carrier 2 in the third temperature (S17). Then, in a third rising step, the temperature control module raises the temperature of the rotational carrier 2 to the first temperature (S18).

Figure 7B:
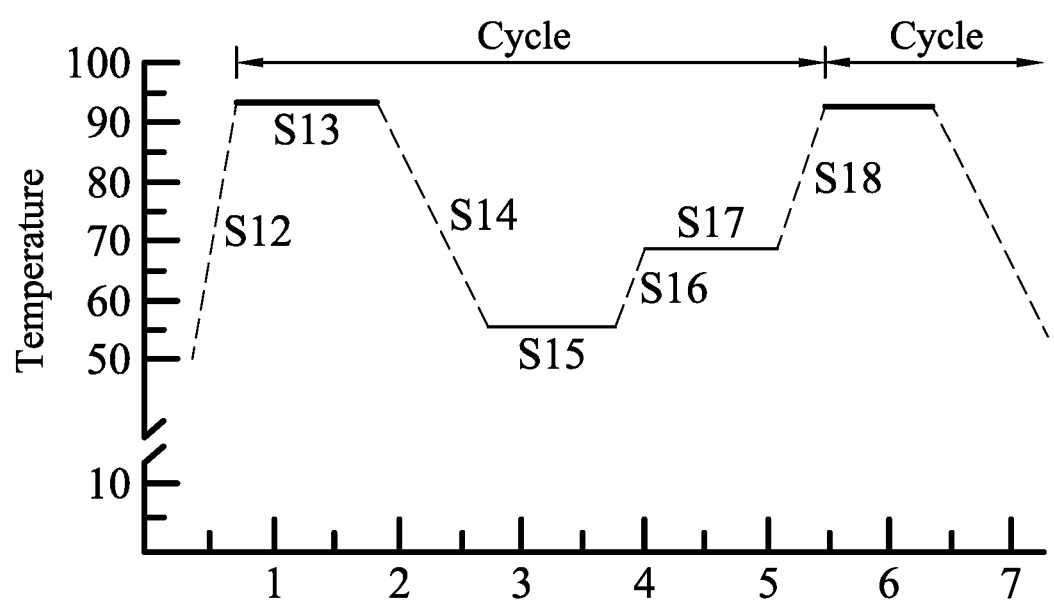
FIGS. 7B and 7C show a specific embodiment of the molecular diagnostics method of the embodiment of the invention.
Figure 7C:
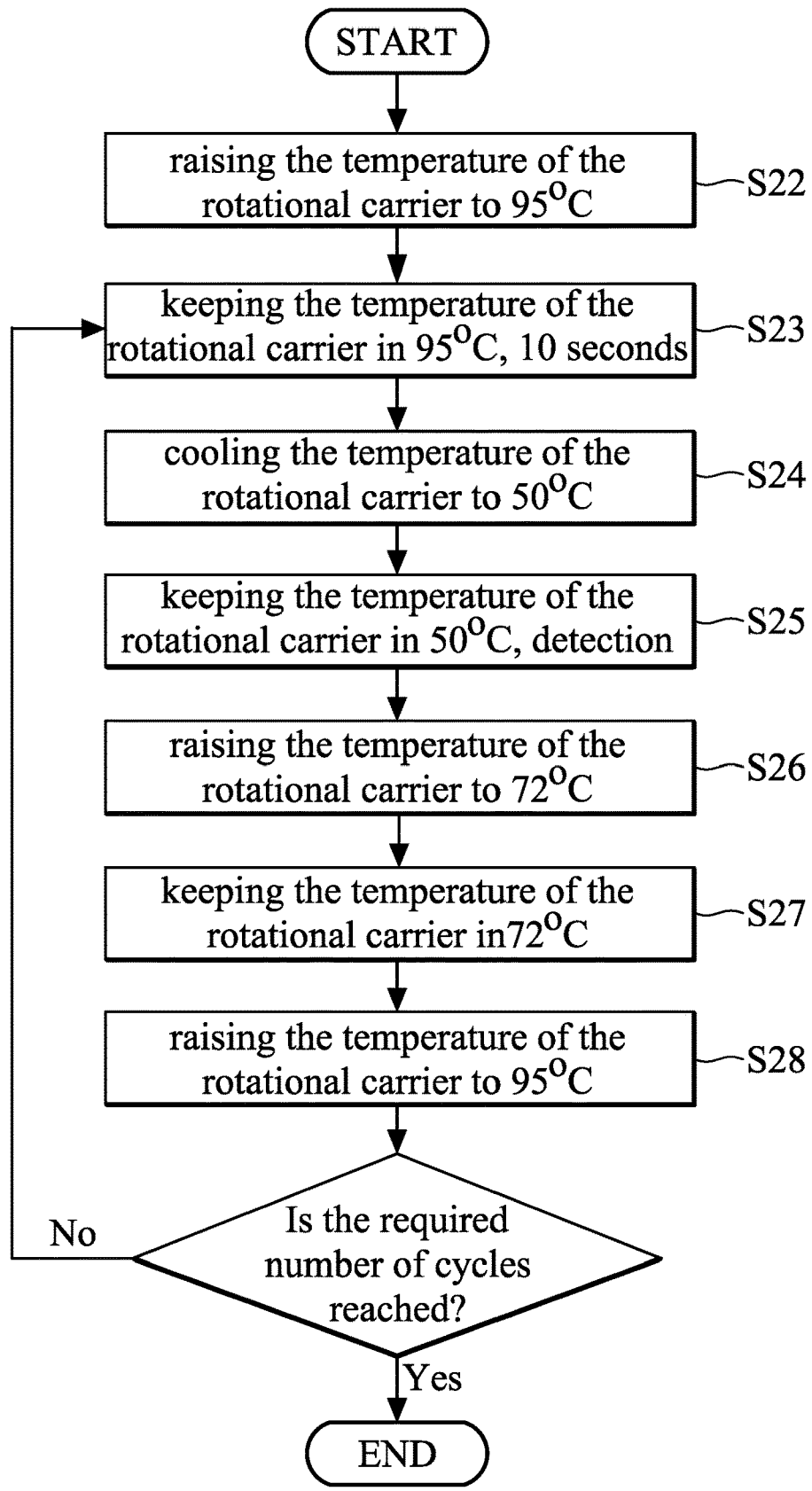

FIGS. 7B and 7C show a specific embodiment of the molecular diagnostics method of the embodiment of the invention. With reference to FIGS. 7B and 7C, in a first rising step, the temperature control module raises the temperature of the rotational carrier 2 to a first temperature (95° C.) (S22). Then, in a first maintaining step, the temperature control module keeps the temperature of the rotational carrier 2 in the first temperature (95° C., 10 seconds) (S23). Next, in a first cooling step, the temperature control module cools the temperature of the rotational carrier 2 to a second temperature (50° C.) (S24). Then, in a detection step, the temperature control module keeps the temperature of the rotational carrier 2 to the second temperature (50° C., detection) (S25). Next, in a second rising step, the temperature control module raises the temperature of the rotational carrier 2 to a third temperature (72° C.) (S26). Then, in a second maintaining step, the temperature control module keeps the temperature of the rotational carrier 2 in the third temperature (72° C.) (S27). Then, in a third rising step, the temperature control module raises the temperature of the rotational carrier 2 to the first temperature (95° C.) (S28). Before the required number of cycles is reached, the effect of gene amplification can be obtained by repeating steps S13 to S18. After the required number of cycles is reached, the process ends.

In one embodiment of the invention, in the first rising step, the first maintaining step, the first cooling step, the second rising step, the second maintaining step and/or the third rising step, the temperature detection control unit 34 sends the power storage data via the first wireless transmission unit 331. The system processing unit 12 receives the power storage data via the second wireless transmission unit 11, and determines whether the molecular diagnostics apparatus has entered the charging mode according to the power storage data.

In the detection step, the molecular diagnostics apparatus enters a detection mode. In the detection mode, the optical system O detects the sample, and the motor R1 rotates the rotational carrier 2 at a detection speed. In the charging mode, the motor R1 rotates the rotational carrier 2 at a charging speed. The charging speed is faster than the detection speed.

In the embodiments of the invention, in the detection mode, the motor R1 must rotate the rotational carrier 2 in the detection speed, and the optical system O can detect the sample under the detection speed. Therefore, the temperature detection control unit 34 cannot be charged in the detection mode. However, in the first rising step, the first maintaining step, the first cooling step, the second rising step, the second maintaining step and the third rising step, the rotation speed of the rotational carrier 2 does not affect the processes for raising, maintaining, or dropping the temperature. Thus, the molecular diagnostics apparatus detects the power storage in the first rising step, the first maintaining step, the first cooling step, the second rising step, the second maintaining step and the third rising step, and determines whether the molecular diagnostics apparatus shall enter the charging mode.

As mentioned above, in other words, in any step of the first rising step, the first maintaining step, the first cooling step, the detection step, the second rising step, the second maintaining step, and the third rising step, the molecular diagnostics apparatus can be in the feedback mode at any time (step). Additionally, in any step of the first rising step, the first maintaining step, the first cooling step, the second rising step, the second maintaining step, and the third rising step, rather than (except) the detection step, the molecular diagnostics apparatus can enter the charging mode at any time (step).

Utilizing the molecular diagnostics apparatus of the embodiment of the invention, the detection module is charged by principle of magnetic field induction. The conventional signal cable and power cable are omitted. The structure of the molecular diagnostics apparatus is simplified. The reliability of the signal transmission and power transmission can be improved.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term).

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A molecular diagnostics apparatus, adapted to perform DNA chain replication to one sample, comprising:
   a bracket;
   a central control module, disposed on the bracket;
   a motor, disposed on the bracket, wherein the central control module drives the motor;
   a magnetic unit, disposed on the bracket, wherein the magnetic unit provides a magnetic field;
   a rotational carrier, wherein the motor is adapted to rotate the rotational carrier, the rotational carrier is rotated relative to the bracket, and the sample is disposed on the rotational carrier;
   a detection module, disposed on the rotational carrier; and
   at least one power supply coil, coupled to the detection module, and disposed on the rotational carrier,
   wherein in a charging mode, the central control module drives the motor to rotate the rotational carrier, the power supply coil generates a first induced current according to the magnetic field, and the first induced current is supplied to the detection module.

2. The molecular diagnostics apparatus as claimed in claim 1, wherein the rotational carrier further comprises a holder and at least one coil mounting member, the detection module is disposed on the holder, the power supply coil is disposed on the coil mounting member, and the coil mounting member is connected to the holder.

3. The molecular diagnostics apparatus as claimed in claim 2, wherein the holder is on a virtual flat plane, the coil mounting member is on a virtual curved plane, and the virtual curved plane is orthogonal to the virtual flat plane.

4. The molecular diagnostics apparatus as claimed in claim 2, further comprising an optical system, wherein the optical system is affixed to the bracket, and the power supply coils surround the optical system.

5. The molecular diagnostics apparatus as claimed in claim 4, wherein the magnetic unit comprises an N-pole magnet and an S-pole magnet, and the optical system and the power supply coils are located between the N-pole magnet and the S-pole magnet.

6. The molecular diagnostics apparatus as claimed in claim 4, further comprising a temperature control module, wherein the temperature control module is adapted to control a temperature of the rotational carrier, the detection module comprises a temperature detection module, and the temperature detection module detects the temperature of the rotational carrier and generates a temperature data.

7. The molecular diagnostics apparatus as claimed in claim 6, wherein the rotational carrier comprises a plurality of receiving recesses, the receiving recesses are arranged annularly around an axis of the rotational carrier, and the sample is adapted to be disposed in one of the receiving recesses.

8. The molecular diagnostics apparatus as claimed in claim 1, further comprising an upper cover and an upper cover display module, wherein the upper cover display module is disposed on the upper cover, the detection module comprises a detection module coil, the upper cover display module comprises a display module coil, the detection module coil provides an induced electromotive force (electromagnetic field), the display module coil generates a second induced current according to the induced electromotive force (electromagnetic field), and the second induced current is supplied to the upper cover display module.

9. The molecular diagnostics apparatus as claimed in claim 1, wherein the detection module comprises a rectifier, an energy storage unit, a first wireless transmission unit, a temperature detection control unit, and a temperature sensing unit, the rectifier is coupled to the power supply coil and the energy storage unit, the temperature detection control unit is coupled to the temperature sensing unit and the first wireless transmission unit, wherein in the charging mode, the power supply coil generates the first induced current, the first induced current passes through the rectifier and charges the energy storage unit, the energy storage unit provides power to the detection module, wherein in a feedback mode, the temperature sensing unit detects the temperature of the rotational carrier and generates temperature data, the temperature detection control unit sends the temperature data to the first wireless transmission unit, and the first wireless transmission unit sends the temperature data.

10. The molecular diagnostics apparatus as claimed in claim 9, wherein the central control module comprises a second wireless transmission unit, a system processing unit, and a motor driving unit, the system processing unit is coupled to the second wireless transmission unit and the motor driving unit, wherein in the charging mode, the system processing unit controls the motor via the motor driving unit, the motor rotates the rotational carrier, and the power supply coil generates the first induced current according to the magnetic field, wherein in the feedback mode, the second transmission unit receives the temperature data sent from the first wireless transmission unit, and the temperature data is transmitted to the system processing unit.

11. The molecular diagnostics apparatus as claimed in claim 10, wherein the detection module further comprises a memory unit, the temperature data is stored in the memory unit, and the temperature detection control unit reads the temperature data from the memory unit and sends the temperature data to the first wireless transmission unit.

12. A molecular diagnostics method, adapted to perform DNA chain replication to one sample, comprising:
   providing the molecular diagnostics apparatus of claim 1;
   providing an optical system of the molecular diagnostics apparatus, wherein the optical system is affixed to the bracket, and the power supply coils are surrounding the optical system; and
   providing a temperature control module of the molecular diagnostics apparatus, wherein the temperature control module is adapted to control the temperature of the rotational carrier, the detection module detects the temperature of the rotational carrier and generates temperature data,
   wherein in a charging mode, the central control module drives the motor to rotate the rotational carrier, the power supply coil generates a first induced current according to the magnetic field, and the first induced current is supplied to the detection module.

13. The molecular diagnostics method as claimed in claim 12, wherein the detection module comprises a rectifier, an energy storage unit, a first wireless transmission unit, a temperature detection control unit and a temperature sensing unit, the rectifier is coupled to the power supply coil and the energy storage unit, the temperature detection control unit is coupled to the temperature sensing unit and the first wireless transmission unit, wherein in the charging mode, the power supply coil generates the first induced current, the first induced current passes through the rectifier and charges the energy storage unit, the energy storage unit provides power to the detection module, wherein in a feedback mode, the temperature sensing unit detects the temperature of the rotational carrier and generates temperature data, the temperature detection control unit sends the temperature data to the first wireless transmission unit, and the first wireless transmission unit sends the temperature data.

14. The molecular diagnostics method as claimed in claim 13, wherein the central control module comprises a second wireless transmission unit, a system processing unit, and a motor driving unit, the system processing unit is coupled to the second wireless transmission unit and the motor driving unit, wherein in the charging mode, the system processing unit controls the motor via the motor driving unit, the motor rotates the rotational carrier, and the power supply coil generates the first induced current according to the magnetic field, wherein in the feedback mode, the second transmission unit receives the temperature data sent from the first wireless transmission unit, and the temperature data is transmitted to the system processing unit.

15. The molecular diagnostics method as claimed in claim 14, wherein the detection module further comprises a memory unit, the temperature data is stored in the memory unit, and the temperature detection control unit reads the temperature data from the memory unit and sends the temperature data to the first wireless transmission unit.

16. The molecular diagnostics method as claimed in claim 14, further comprising:
   in a first rising step, the temperature control module raises the temperature of the rotational carrier to a first temperature;
   in a first maintaining step, the temperature control module keeps the temperature of the rotational carrier at the first temperature;
   in a first cooling step, the temperature control module cools the temperature of the rotational carrier to a second temperature;
   in a detection step, the temperature control module keeps the temperature of the rotational carrier at the second temperature;
   in a second rising step, the temperature control module raises the temperature of the rotational carrier to a third temperature;
   in a second maintaining step, the temperature control module keeps the temperature of the rotational carrier at the third temperature; and
   in a third rising step, the temperature control module raises the temperature of the rotational carrier to the first temperature.

17. The molecular diagnostics method as claimed in claim 16, wherein in the first rising step, the first maintaining step, the first cooling step, the second rising step, the second maintaining step, and the third rising step, the temperature detection control unit sends power storage data via the first wireless transmission unit, and the system processing unit receives the power storage data via the second wireless transmission unit and determines whether the molecular diagnostics apparatus has entered the charging mode according to the power storage data.

18. The molecular diagnostics method as claimed in claim 16, wherein in the detection step, the molecular diagnostics apparatus enters a detection mode, wherein in the detection mode, the optical system detects the sample, and the motor rotates the rotational carrier at a detection speed.

19. The molecular diagnostics method as claimed in claim 18, wherein in the charging mode, the motor rotates the rotational carrier at a charging speed, and the charging speed is faster than the detection speed.

20. The molecular diagnostics method as claimed in claim 16, wherein the molecular diagnostics apparatus can be in the feedback mode in any step of the first rising step, the first maintaining step, the first cooling step, the detection step, the second rising step, the second maintaining step, and the third rising step.

\* \* \* \* \*